United States Patent [19]

Peers-Trevarton et al.

[11] 4,301,805
[45] Nov. 24, 1981

[54] CARDIAC PACER CONNECTOR SYSTEM

[75] Inventors: Charles A. Peers-Trevarton, Coral Springs; Peter P. Tarjan, Miami; Stephen F. Vadas, Homestead; Frederick S. Dorman, Boca Raton, all of Fla.

[73] Assignee: Cordis Corporation, Miami, Fla.

[21] Appl. No.: 173,640

[22] Filed: Jul. 30, 1980

[51] Int. Cl.³ .............................................. A61N 1/00
[52] U.S. Cl. ................................................ 128/419 P
[58] Field of Search .......... 128/419 P, 419 PG, 419 PS

[56] References Cited

U.S. PATENT DOCUMENTS

| 3,253,595 | 5/1966 | Murphy, Jr. | 128/419 |
| 3,518,997 | 7/1970 | Sessions | 128/419 PS |
| 3,735,766 | 5/1973 | Bowers, et al. | 128/419 P |
| 4,072,154 | 2/1978 | Anderson et al. | 128/419 P |
| 4,105,037 | 8/1978 | Richter et al. | 128/419 P |
| 4,142,532 | 3/1979 | Ware | 128/419 P |
| 4,236,525 | 12/1980 | Slugtz et al. | 128/419 P |

FOREIGN PATENT DOCUMENTS 1423262  2/1976  United Kingdom .

Primary Examiner—William E. Kamm
Attorney, Agent, or Firm—Kenway & Jenney

[57] ABSTRACT

A cardiac pacer employing the connector system disclosed herein is usable with either a unipolar lead or a bipolar lead provided with a plug at the proximal end having an extending pin portion to which a distal stimulating electrode is electrically connected. In the case of a bipolar electrode, an annular ring is provided on the plug to which the reference or indifferent electrode is connected. Respective clamping means are provided for establishing electrical connections to the pin and the annular ring, if present. A bridging means is provided for utilizing the pacer case as a reference potential when a unipolar lead is being used.

4 Claims, 4 Drawing Figures

CARDIAC PACER CONNECTOR SYSTEM

BACKGROUND OF THE INVENTION

The present invention relates to a connector system for cardiac pacers and pacer leads and more particularly to such a system which permits the use of either a unipolar or bipolar lead.

In connection with the development of electrical cardiac pacing systems which stimulate a patient's heart to replace or supplement natural stimulation, a great variety of electrode systems have been developed for applying electrical energy to the patient's heart muscle. In general, these electrode or lead systems may be divided into two different categories. First, there are bipolar leads in which the lead itself carries two electrodes. One electrode is a stimulating electrode usually located at the distal tip of the elongate lead structure, and the other is a reference or indifferent electrode usually in the form of an annular conductive band spaced away from the distal tip of the lead. With such a bipolar electrode, current thus typically flows a relatively short distance in the patient's body. The second category includes unipolar leads. A unipolar lead includes but a single conductor terminating with the stimulating electrode at the distal end of the lead. The proximal end of the lead is connected to one side of the pulse generating circuitry within the pacer. A reference or indifferent potential is established by connecting the other side of the pulse-generating circuitry to a conductive wall of the pacer case which serves as the reference electrode. The pacer case itself is typically implanted some distance from the patient's heart, e.g., in the abdomen or in a subcutaneous pocket near the patient's shoulder. While the use of the pacer case affords a very large area of contact with the patient's body, the stimulating and sensing current path is relatively long.

Depending on circumstances, one or the other of these two general classes of electrode lead systems may be preferred. The same pacer electronics may, however, be usable in either case. It is thus highly advantageous to provide a system of interfacing the pacer electronics with the lead system in a manner which is flexible and can accommodate leads of either type. As will be understood, such an interfacing system minimizes the need for largely duplicative stocking and simplifies the replacement of pacer electronics at the end of battery life.

Among the several objects of the present invention may be noted the provision of a cardiac pacer incorporating a connector system which is usable with either a unipolar lead or a bipolar lead; the provision of such a system which permits the pacer case to be selectively utilized as an indifferent electrode; the provision of such a system which facilitates reliable connections to the lead utilized; the provision of such a system which is highly reliable and which is of relatively simple and inexpensive construction. Other objects and features will be in part apparent and in part pointed out hereinafter.

SUMMARY OF THE INVENTION

A cardiac pacer in accordance with the present invention incorporates a connector system usable with either a unipolar lead having a single distal electrode or a bipolar lead having both a distal electrode and a reference electrode, both types of lead incorporating at the proximal end thereof a generally cylindrical plug having an extending pin portion to which the distal electrode is electrically connected. The plug of the bipolar electrode has an annular ring to which the reference electrode is connected. The pacer itself incorporates a pulse generator including an output circuit having a first side and a second side together with batteries for powering the pulse generator. These components are enclosed in a casing having at least one conductive wall. A first clamping means is provided for establishing an electrical connection to the pin extending from the lead plug, the first clamping means being connected to one side of the output circuit. A second clamping means is provided for establishing an electrical connection to the annular ring on the plug. Selectively operable bridging means are provided having a first part connected to the other side of the output circuit, a second part connected to the case wall, and a third part connected to the second clamping means. Accordingly, in the absence of a reference electrode on the lead, the bridging means may be operated to connect the first and second parts so that the case wall is employed as the reference potential for the distal electrode. When a reference electrode is present on the lead, the bridging means may be operated to connect the first and third parts so that the reference electrode is electrically connected to the other side of the output circuit.

In a preferred embodiment the bridging means includes an electrically conductive set screw threadably attached to the first part of the bridging means and adapted for selectively contacting either the second or third part of the bridging means. In this embodiment, the first and second clamping means comprise set screws.

BRIEF DESCRIPTION OF THE DRAWINGS

The invention disclosed herein will be understood better with reference to the following drawings in which.

DESCRIPTION OF THE PREFERRED EMBODIMENT

Figure 1:
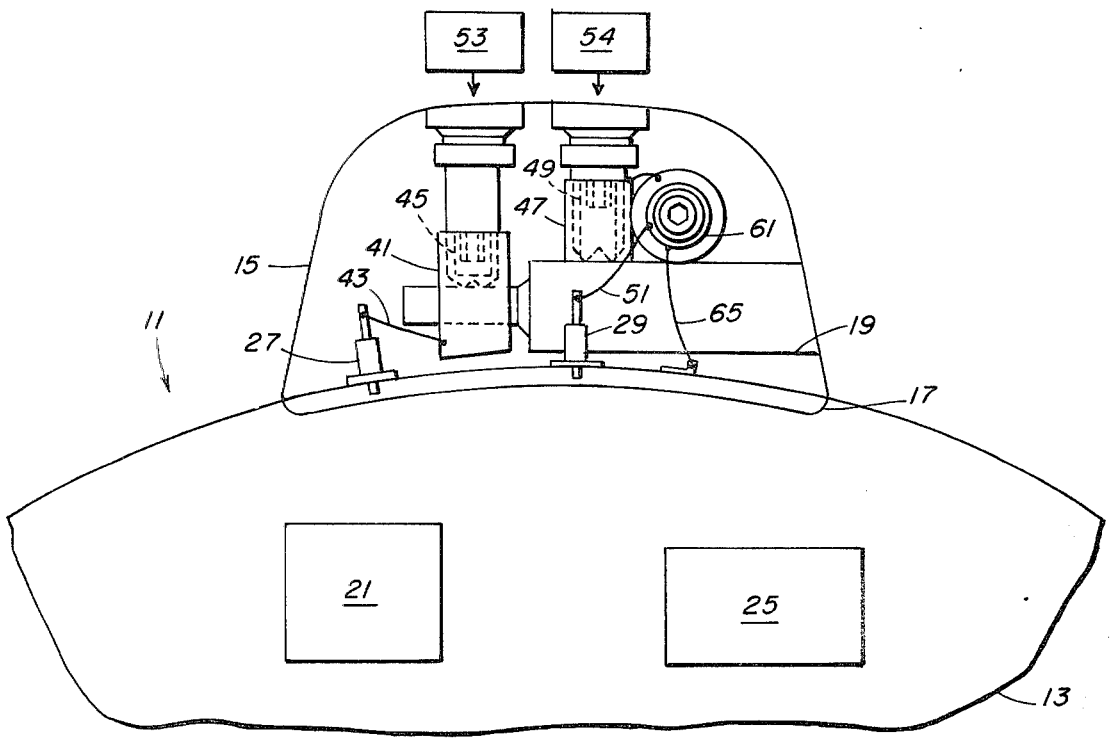
FIG. 1 is a diagrammatic representation of a cardiac pacing device.
Figure 2:
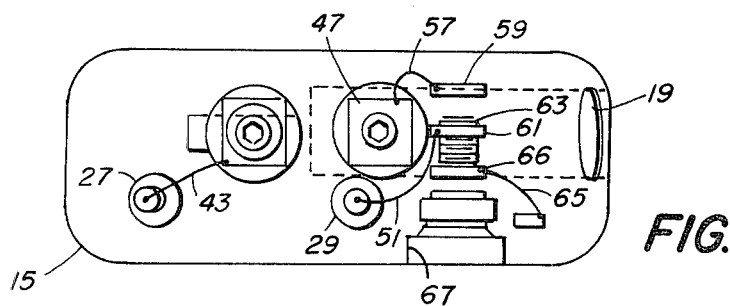
FIG. 2 is a diagrammatic representation of the connector system of this invention.

Referring now to FIGS. 1 and 2, a cardiac pacer employing a connector system in accordance with the present invention is indicated generally by reference character 11. Pacer 11 comprises a generally disk-shaped case 13, having on one side a so-called neck portion 15 which comprises the connector components. Case 13 comprises a metallic casing 17 which encloses the electronic components such as the pulse-generating circuitry, indicated generally by reference character 21, and batteries 25. Casing 17 is hermetically sealed with electrical connections being brought out through feed-through terminals 27 and 29. The neck 15 is preferably cast from a clear insulating plastic resin and adhesively as well as mechanically bonded to the case 13.

Figure 3:
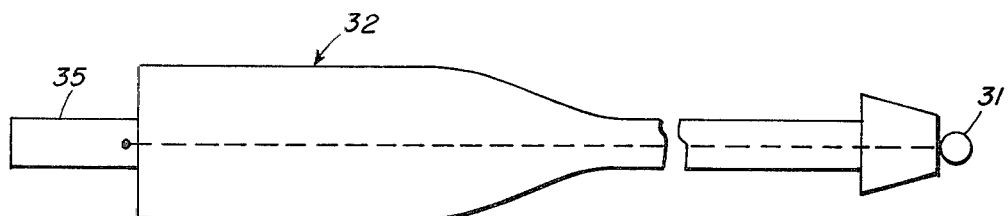
FIG. 3 is a diagrammatic representation of a unipolar lead.
Figure 4:
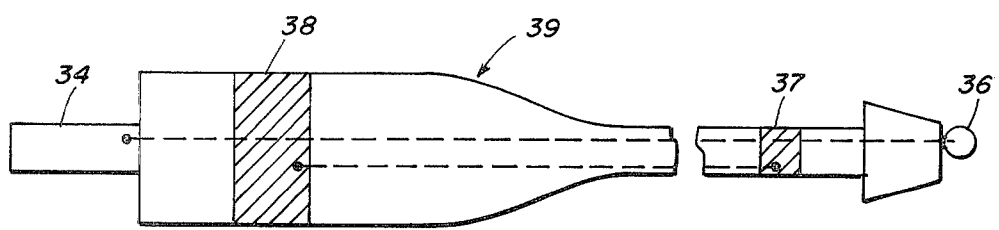
FIG. 4 is a diagrammatic representation of a bipolar lead.

Representative leads adapted for use with the pacer of FIGS. 1 and 2 are illustrated in FIGS. 3 and 4. The lead illustrated in FIG. 3 is a unipolar lead, having at its distal end a conventional ball electrode 31 adapted for stimulating the ventricle of a patient's heart, access thereto having been had through one of the major veins. A generally cylindrical plug 32 is provided at the proximal end of the lead, the plug having a projecting pin 35 to which the distal electrode 31 is connected through a flexible conductor.

A bipolar lead is illustrated in FIG. 4. While this lead also incorporates a distal electrode 36 electrically connected to a projecting pin 34, it also provides an annular or ring-like electrode 37 spaced several inches from the distal tip electrode. The annular electrode is connected, as indicated, to an annular ring 38 on the plug 39. While parallel conductors connecting the respective electrodes are shown, it should be understood that coaxial conductors could in fact be preferred in order to minimize sensitivity to external electromagnetic sources.

The pacer neck 15 includes a socket 19 for receiving either of the plugs 32 or 39. Molded into the neck 15 is a first metallic terminal block 41 through which the tip of the lead plug extends. This block 41 is electrically connected by a wire 43 to the feedthrough 27. Threaded into the terminal block 41 is a set screw 45 which, when tightened, clamps and establishes a very secure electrical contact with the plug projecting pins 34 or 35.

Also cast into the neck 15 is a second terminal block 47 carrying a similar set screw 49. The terminal block 47 is positioned within the neck so that the set screw 49 is adapted to clamp down upon and establish electrical connection to the annular electrode 38 on the lead plug 39 when a bipolar mode of operation is desired. Access to the set screws 45 and 49 is obtained through corresponding openings in the top of the neck which can be closed by sealing plugs 53 and 54, as indicated, after the connection is secured.

As may best be seen in FIG. 2, the terminal block 47 is also electrically connected, by means of a lead 57, to a fixed contact 59 which forms one part of a selectively operable circuit bridging system. Another portion of the bridging system is a block 61 carrying a set screw 63. The block 61 is electrically connected, by means of a lead 51 to the feedthrough terminal 29. A third portion of the bridging system is a fixed block 66 which is connected electrically to the pacer case 17 by means of a wire 65.

When it is desired to use the illustrated pacer with a bipolar lead such as that shown in FIG. 4, the plug 39 is inserted into the socket 19 and the set screws 45 and 49 are tightened down so that a very secure contact is made with the pin 34 and the annular ring 38, respectively. The bridging device is then operated so that set screw 63 contacts the fixed contact 59. Thus, the pacer case remains isolated from the output circuitry of the pulse generator. This arrangement then is suitable for bipolar pacing in which the pacer case does not perform an electrically active role, but rather stimulation is effected between the distal electrode 36 and the annular electrode 37 on the lead itself.

To effect unipolar stimulation, a lead such as that illustrated in FIG. 3 is employed, the plug 32 being inserted in the socket 19. In this case, only the set screw 45 need be tightened down to establish an electrical connection. Set screw 49 is taken out or left not tightened. In the case of unipolar pacing, the set screw 63 is rotated to establish a bridging connection between the fixed block 66 which is connected to the pacer case 17 and the block 61 which is connected to the feedthrough 29. By this arrangement, a secure and continuous electrical connection is made from one side of the pulse generating circuitry, through the feedthrough 29, and thence to the pacer case 17. This condition is illustrated in FIG. 2. Accordingly, the arrangement is appropriate for unipolar stimulation in which the pacer case itself acts as a reference or indifferent potential for the distal stimulating electrode 31 at the tip of a unipolar pacing lead.

In some circumstances, it may be desirable to change the mode of operation of the pacer/lead system to a unipolar mode even though a bipolar lead has previously been implanted. The flexibility of the present connector system permits this since the presence of the second (indifferent) electrode on the lead itself can be ignored if the set screw 63 is rotated out so that the block 61 is connected to the block 66 thereby bringing the pacer case 17 into operation as the reference or indefinite electrode so that a unipolar mode of operation is obtained, even though the lead structure itself provides for bipolar operation.

To prevent body fluids from contacting the bridging system disclosed herein thereby to eliminate the possibility of a short circuit, a recess 67 providing access to the bridging set screw 63 may be sealed with a suitable plug (not shown). In addition, it may be desirable to fill the region between the fixed contact 59 and the fixed terminal block 66 with oil to prevent the entry of body fluids. In this case, the bridging set screw 63 is provided with a longitudinal hole (not shown) so that the oil may flow through screw 63 as it is operated between the fixed contact 59 and the fixed terminal block 66.

In view of the foregoing, it may be seen that the several objects of the present invention are achieved and other advantageous results have been attained.

As various changes could be made in the above constructions without departing from the scope of the invention, it should be understood that all matter contained in the above description or shown in the accompanying drawings shall be interpreted as illustrative and not in a limiting sense.

What is claimed is:

1. A cardiac pacer incorporating a connector system usable with either a unipolar lead having a single distal electrode or a bipolar lead having both a distal electrode and a reference electrode, both types of lead incorporating at the proximal end thereof a generally cylindrical plug having an extending pin portion to which the distal electrode is electrically connected, the plug of the bipolar lead having an annular ring to which the reference electrode is electrically connected; said pacer comprising:

pulse generator means including an output circuit having a first side and a second side;

batteries for powering said pulse generator means;

a casing for said batteries and said pulse generator means including at least one conductive case wall;

a first clamping means for establishing an electrical connection to said pin extending from said plug, said first clamping means being connected to one side of said output circuit;

a second clamping means for establishing an electrical connection to said annular ring on said plug; and selectively operable electrical bridging means having a first part connected to the other side of said output circuit, a second part connected to said case wall, and a third part connected to said clamping means whereby, in the absence of a reference electrode on said lead, said bridging means may be operated to connect said first part and said second part so that said case wall is employed as a reference potential for the distal electrode; and whereby, in the presence of a reference electrode on said lead, said bridging means may be operated to connect said first part and said third part so that said reference electrode is electrically connected to the other side of said output circuit.

2. The pacer of claim 1 wherein said bridging means comprises an electrically conductive screw threadably attached to said first part of said bridging means and adapted for selectively contacting said second part of said bridging means or said third part of said bridging means.

3. The pacer of claim 1 wherein said first clamping means comprises a set screw adapted for securely contacting said pin.

4. The pacer of claim 1 wherein said second clamping means comprises a set screw adapted for securely contacting said annular ring.

* * * * *